United States Patent [19]

Stanko

[11] Patent Number: 5,480,909
[45] Date of Patent: Jan. 2, 1996

[54] METHOD FOR INHIBITING GENERATION OF FREE-RADICALS

[75] Inventor: Ronald T. Stanko, Pittsburgh, Pa.

[73] Assignee: University of Pittsburgh Medical Center, Pittsburgh, Pa.

[21] Appl. No.: 286,946

[22] Filed: Aug. 8, 1994

[51] Int. Cl.⁶ .......................... A61K 31/19; A61K 31/40; A61K 31/195
[52] U.S. Cl. .......................... 514/557; 514/423; 514/561; 514/563
[58] Field of Search .................................... 514/557, 423, 514/561, 563

[56] References Cited

U.S. PATENT DOCUMENTS

| | | | |
|---|---|---|---|
| 4,158,057 | 6/1979 | Stanko | 424/252 |
| 4,351,835 | 9/1982 | Stanko | 424/252 |
| 4,415,576 | 11/1983 | Stanko | 424/252 |
| 4,548,937 | 10/1985 | Stanko | 424/252 |
| 4,812,479 | 3/1989 | Stanko | 514/557 |
| 4,874,790 | 10/1989 | Stanko | 514/557 |
| 5,134,162 | 7/1992 | Stanko | 514/557 |
| 5,256,697 | 10/1993 | Miller et al. | 514/625 |
| 5,294,641 | 3/1994 | Stanko | 514/540 |

OTHER PUBLICATIONS

DeBoer et al, Am. J. Physiol 265 (Heart Circ. Physiol 34) H1571–H1576; 1993.
O'Donnell–Tormey et al., J. Exp. Med. (1987 Feb.) vol. 165, (2), pp. 500–514.
Stanko et al Pyruvate Inhibits Growth of Mammary Adenocarcinoma 13762 in Rats, Cancer Research 54, 1004–1007, 1994.

*Primary Examiner*—Allen J. Robinson
*Attorney, Agent, or Firm*—Harry B. Keck

[57] ABSTRACT

Certain incidents in mammals trigger the generation of free-radicals which are associated with cell death. Animals experiencing such medical incidents are dosed with pyruvate salts or esters in an amount of 5 to 20 weight percent of the total carbohydrate intake. The dosage of pyruvate may be provided to the animal before the medical incident, during the medical incident and after the medical incident. In addition to the known property in pyruvate for scavenging free-radicals, this disclosure points out the unexpected effectiveness of pyruvate as an inhibitor of free-radical generation.

7 Claims, 2 Drawing Sheets

METHOD FOR INHIBITING GENERATION OF FREE-RADICALS

BACKGROUND OF THE INVENTION

1. Field of the Invention

This invention relates to the use of pyruvate to inhibit generation of free-radicals in a mammal.

2. Description of the Prior Art

Pyruvate has been described for use in retarding fatty deposits in livers (U.S. Pat. No. 4,158,0571); for diabetes treatment (U.S. Pat No. 4,874,790); for retarding weight main (U.S. Pat. Nos. 4,812,479, 4,548,937, 4,351,835); to increase body protein concentration in a mammal (U.S. Pat. No. 4,415,576); for treating cardiac patients to increase the cardiac output without accompanying increase in cardiac oxygen demand (U.S. Pat. No. 5,294,641); for extending athletic endurance (U.S. Pat. No. 4,315,835); for retarding cholesterol increase (U.S. Pat. No. 5,134,162); and for inhibiting growth in spread of malignancy and retarding DNA breaks (Application Ser. No. 08/194.857. filed Feb. 14, 1994).

Pyruvate has been reported as a free radical scavenger, De Boer, L. W. V. et al, Am. J. Physiol 265 (Heart Circ. Physiol 341): H1571–H11576, 1993.

FREE-RADICAL PHENOMENON

Free-radicals have been identified in mammals as an accompaniment to cell death. Several free-radical scavengers have been promoted for use to neutralize free-radicals and prevent them from adversely affecting living cells. Examples are vitamin C. vitamin E, beta-carotene and pyruvate. These free-radical scavengers can be introduced into a patient orally or parenterally in appropriate carriers, e.g., water or foods. Pyruvate can be provided in edible foods, e.g., cookies, candies, et cetera.

Clofibrate is a pharmaceutical known to generate free-radicals in the liver.

STATEMENT OF THE PRESENT INVENTION

According to this invention, I have discovered that pyruvate not only functions as a free-radical scavenger, but, more importantly, pyruvate inhibits generation of free-radicals. This characteristic appears to be unique among the known free-radical scavengers. The inhibition is measurable, reproducible and credible.

According to this invention, a patient who is experiencing or who is expected to experience bodily stress which might result in free-radical generation receives appropriate dosages of pyruvate before, during and following the free-radical generating incidents. The benefits are that the patient is insulated from the extensive free-radical effects which are normally associated with the patient's medical incidents.

Incidents which generate excess free-radicals include myocardial infarction, diabetes, anoxia, anesthesia, surgery and others. Patient treatment with pyruvate can precede some of those incidents. Other incidents which are detected after the incident may be treated during and following the incident.

Pyruvate is available in several mineral salts, e.g., sodium pyruvate and calcium pyruvate. Pyruvate also is available as pyruvate esters, e.g., U.S. Pat. Nos. 5,283,260 and 5,256.697 specifically pyruvyl-amino acids such as pyruvyl-glycine, pyruvyl-alanine, pyruvyl-leucine, pyruvyl-valine, pyruvyl-isoleucine, pyruvyl-phenyl-alanine, pyruvyl-proline, pyruvyl-sarcosine and their amides. The selected pyruvate can be introduced into the patient parenterally in an appropriate aqueous solution which may also contain other life-sustaining ingredients, e.g., oligosaccharides, fats, minerals, vitamins. The dosage of pyruvate for achieving useful inhibition of free-radical generation is from 5 to 25 weight percent of the patient's carbohydrate diet.

DESCRIPTION OF THE DRAWINGS

FIG. 1 illustrates the value of PALMITOYL CoA OXIDASE, i.e., enzyme production which can be related to $H_2O_2$ generation protein for each group.

FIG. 2 illustrates catalase for each group.

FIG. 3 illustrates the relative intensity of fluorescence, which is a measure of lipofuscin-like-products for each group.

DESCRIPTION OF THE PREFERRED EMBODIMENTS

Figure 1:
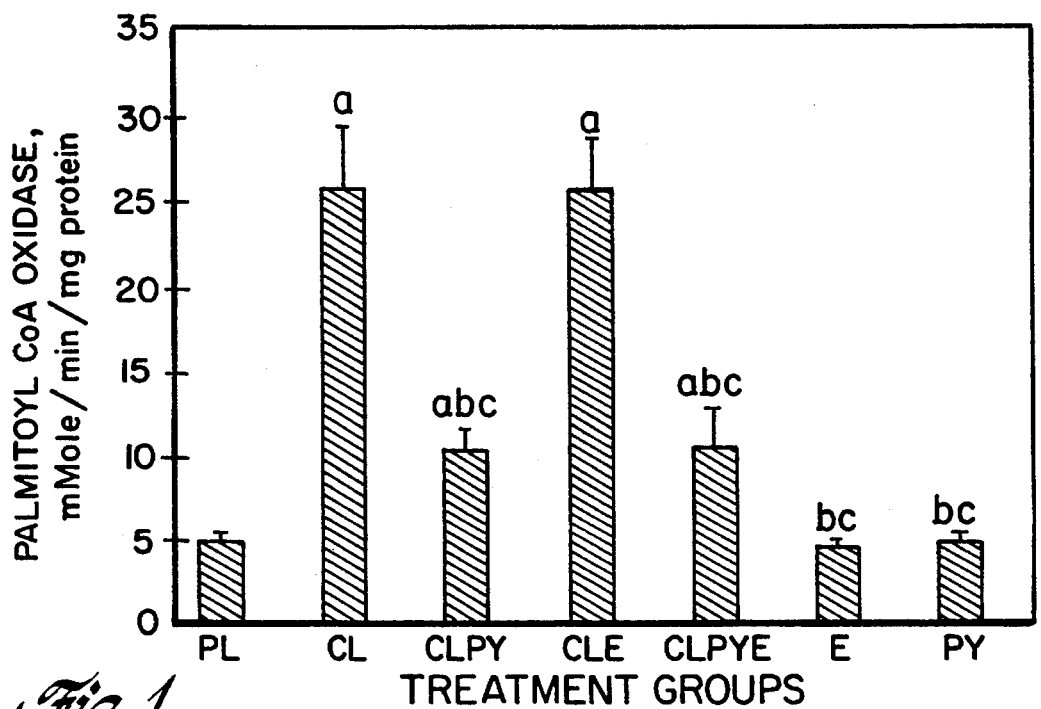
FIGS. 1 through 3 are graphical illustrations of data relating to seven groups of animals.

A series of tests was developed ad hoc to demonstrate the effectiveness of pyruvate in inhibiting free-radical generation. Clofibrate is a pharmaceutical known to generate free-radicals in the liver. The clofibrate causes the patient's beta-peroxidase system to develop peroxisomes and to increase the organelles of the liver. Within the peroxisomes there is beta-oxidation activity which is an enzyme phenomenon whose end products include hydrogen peroxide, which is a free-radical metabolite. The patient's body has a normal defense to free-radicals called catalase. The available catalase cannot neutralize the abnormal generated quality of free-radicals. The surplus free-radicals break down lipid membranes (lipid peroxidation), resulting in cell abnormalities.

With the addition of pyruvate, there is less generation of free-radicals. Peroxisomes do not proliferate when pyruvate is present; beta-oxidation does not increase.

In comparison testing, Vitamin E exhibited its known property of scavenging free-radicals, but did not inhibit generation of free-radicals.

EXAMPLES

Thirty-two male Sprague-Dawley rats weighing approximately 210 grams each were divided into 7 groups and fed a liquid diet (Dyets 710,027, Dyets, Inc., Bethlehem Pa.) for 22 to 26 days. The 7 groups were:

Placebo (PL)—no treatment

Clofibrate (CL)—Clofibrate treatment alone

Clofibrate+Pyruvate (CLPY)—Clofibrate treatment with animals receiving pyruvate

Clofibrate+Vitamin E (CLE)—Clofibrate treatment with animals receiving Vitamin E Clofibrate+Pyruvate+Vitamin E (CLEPY)—Clofibrate treatment with animals receiving pyruvate and Vitamin E Vitamin E (E)—Animals receiving Vitamin E— No Clofibrate Pyruvate (PY)—Animals receiving pyruvate—No Clofibrate Pyruvate was added to the diet as sodium pyruvate (20 grams/liter) and calcium pyruvate (17.9 grams/liter). The pyruvate dosage was 10% of the energy content of the diet of those rats receiving pyruvate. All diets were made isoenergetic by adding polyglucose (Polycosel®, Ross Laboratories, Columbus Ohio) to the diets not containing pyruvate. The sodium and calcium content of the diets were made similar by adding sodium citrate and calcium carbonate to those diets not containing pyruvate. The final composition of all diets was:

| Carbohydrate | 47% |
|---|---|
| Protein | 18% |
| Fat | 35% |
| Energy Content | 0.0042 MJ/ml |

All diets were established to be iso-energetic by calorimetric analysis. Prior to grouping the animals for the experiment, in order to familiarize the animals with the liquid diet, all animals were fed the placebo liquid diet for three days during which time the mean intake was 60 ml/day. Clofibrate was added to the diet to a final concentration of 0.018 gram/liter which is an expected dosage of 0.5 gram/kilogram of initial body weight. Vitamin E was added to the diet to a final concentration of 2 ml/liter, corresponding to a dosage of 30 IU (20 mg/kg) of the initial body weight.

A modified pair technique was employed to assure equal energy intake among the groups. The intake of that group with the smallest intake for a given day (rate-limiting group) was fed to the other groups of animals on the following day and the rate-limiting group intake was fed the next day, et cetera. In most instances the rate-limiting group was CLPY—clofibrate plus pyruvate. The animals for all groups were fed the mean dietary intake for 22 to 26 days (the feeding period). During the feeding period, total intake of clofibrate (TABLE I) and Vitamin E (TABLE II) between the groups was similar.

TABLE I

| | CLOFIBRATE INTAKE |
|---|---|
| GROUP | CLOFIBRATE INTAKE (grams) |
| CL | 3.3 ± 0.1 |
| CLE | 3.3 ± 0.1 |
| CLPY | 3.1 ± 0.1 |
| CLEPY | 3.1 ± 0.1 | p = NS among these groups

TABLE II

| | VITAMIN E INTAKE |
|---|---|
| GROUP | VITAMIN E INTAKE * (International Units) |
| E | 184 ± 5 |
| CLE | 184 ± 5 |
| CLEPY | 173 ± 4 | p = NS among these groups

After 22 days of feeding, one animal from each group was selected for an overnight fast of 16 hours. The selected animals of each group were euthanatized by decapitation (without anaesthesia). For the next 4 days, one animal from each group was selected, fasted, and euthanatized. The liver was obtained from each euthanatized rat for immediate biochemical analysis and prepared for light and electron inicroscope analysis. Blood was obtained from the cervical stump and frozen at −20° C. for later analysis.

BIOCHEMICAL ANALYSIS

A portion of the liver was homogenized in sucrose buffer and analyzed for palmitoyl CoA oxidase and catalase activity and lipofuscin-like products.

STATISTICAL ANALYSIS

Differences between groups were evaluated with a 2-tailed t test. Differences were considered significant with p>0.05. Data are presented as mean±SEM (Standard Error of the Mean) for the animals in each group.

MORPHOLOGIC EVALUATION

Sections of the rat liver were processed for routine histologic analysis by light microscopy and ultrastructural electron microscope evaluation.

As shown in Table III, the animals fed clofibrate alone had a 42% increase in liver size, compared to the placebo. When pyruvate was added to the clofibrate diet (CLPY and CLEPY) the effects of the clofibrate were reduced, i.e., liver size increased 14%, about one-third of the clofibrate alone. Clofibrate plus Vitamin E aggravated the liver size increase to 46%, and Vitamin E along reduced liver weight by 11%.

TABLE III

HEPATIC PARAMETERS

| Group | Liver Weight (g) | Liver Weight/ Body Weight | Protein (mg/g liver) | Protein (mg total) |
|---|---|---|---|---|
| PL | 7.1 ± 0.3 | 0.024 ± 0.001 | 160 ± 6 | 1130 ± 67 |
| CL | 10.1 ± 0.4 | 0.041 ± 0.002 | 211 ± 11 | 2140 ± 160 |
| CLPY | 8.1 ± 0.2 | 0.032 ± 0.001 | 182 ± 8 | 1480 ± 69 |
| CLE | 10.4 ± 0.3 | 0.041 ± 0.001 | 204 ± 9 | 2124 ± 141 |
| CLEPY | 7.5 ± 0.3 | 0.029 ± 0.001 | 172 ± 6 | 1298 ± 81 |
| E | 6.3 ± 0.1 | 0.024 ± 0.001 | 199 ± 10 | 1254 ± 78 |
| PY | 7.4 ± 0.5 | 0.025 ± 0.001 | 170 ± 21 | 1261 ± 166 |

PL = animals fed placebo diet
CL = diet supplemented with clofibrate
CLPY = diet supplemented with clofibrate + pyruvate
CLE = diet supplemented with clofibrate + vitamin E
CLEPY = diet supplemented with clofibrate + pyruvate + vitamin E
E = diet supplemented with vitamin E
PY = diet supplemented with pyruvate The protein content of the liver was significantly increased by clofibrate (from 1130 grams to 2140 grams) and almost completely normalized by pyruvate (from 1130 grams to 1480 grams). Interestingly the vitamin E supplementation of the clofibrate diet had no effect on the clofibrate-induced liver size and protein change (compare 2140 grams and 2124 grams). Similarly adding vitamin E to the clofibrate and pyruvate group did not significantly alter the results (compare 1298 grams and 1480 grams), indicating that the vitamin E supplementation did not appreciably enhance the normalizing effect of the pyruvate.

BETA-OXIDATION

FIG. 1 shows the hepatic peroxisomal beta-oxidation activity (nmol/min/mg protein). The clofibrate induced a five-fold increase in activity of the peroxisomal enzyme system, indicating significant free-radical generation. Pyruvate reduced the clofibrate-enhanced increases in beta-oxidation by 75%, indicating substantial inhibition of free-radical generation. Vitamin E did not inhibit the effects of clofibrate on the enzyme system. Vitamin E (CLEPY) did not enhance the normalizing effects of pyruvate (CLPY).

Figure 2:
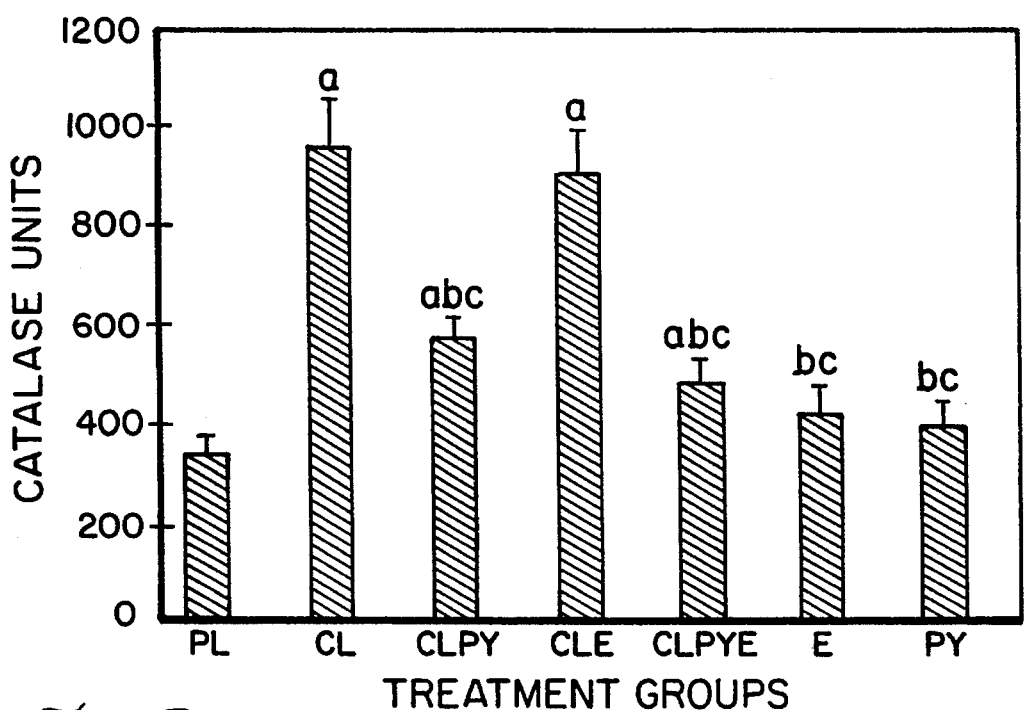
Figure 3:
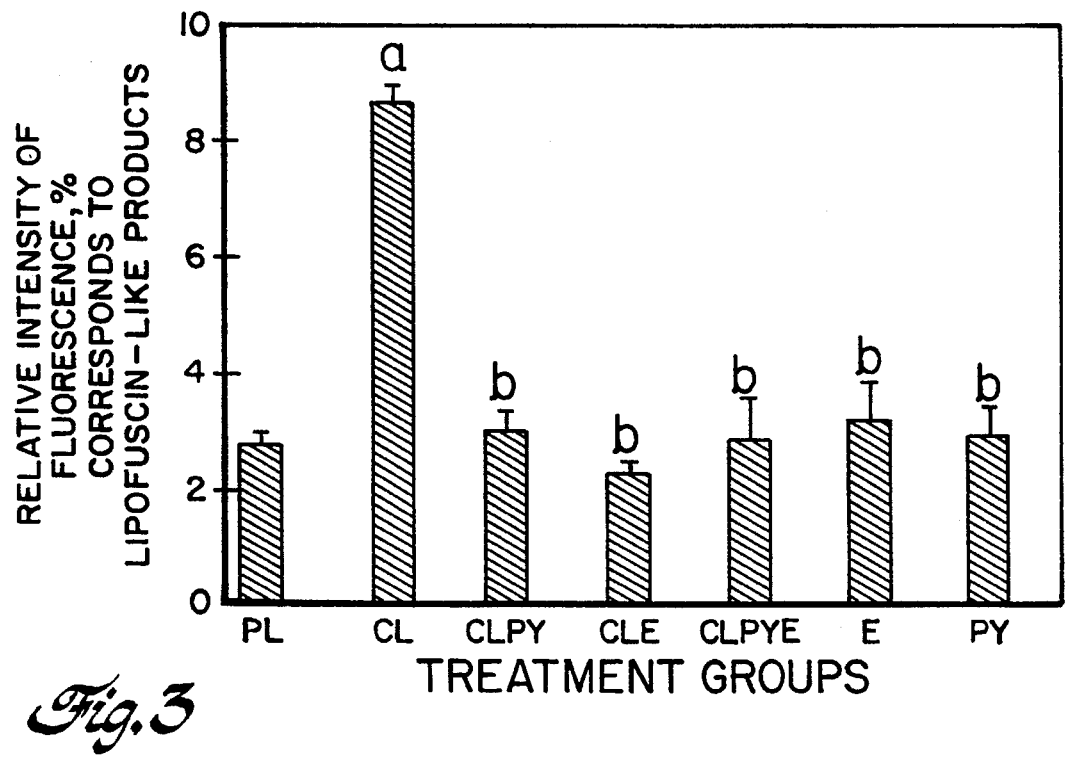

NOTE: In FIGS. 1, 2, 3, the lower-case letters a, b, c indicate a=p<0.05 vs. PL b=p<0.05 vs. CL c=p<0.05 rs. CLE

CATALASE ACTIVITY

FIG. 2 illustrates that the catalase activity increased nearly three-fold with clofibrate, indicating free-radical generation. Addition of vitamin E (CLE) did not significantly reduce the catalase activity. The animals fed pyruvate in addition to clofibrate (CLPY and CLEPY) increased the activity by one-half or less, indicating inhibition of the free-radical generation.

LIPOFUSCIN-LIKE PRODUCTS

The relevant fluorescent intensity of lipofuscin-like-products is shown in FIG. 3. Clofibrate induced a three-fold increase in lipofuscin-like products. The increase of lipofuscin-like products was retarded completely by the addition of pyruvate or vitamin E to the clofibrate diets. Thus the Vitamin E effectively scavenged free-radicals which would have caused lipofuscin-like-product. The pyruvate likewise retarded free-radical presences, partly by inhibiting generations and partly by scavenging the free-radicals that were generated. The significance of FIG. 3 is that limofuscin-like-products are present and measurable if the body contains free-radicals.

CONCLUSIONS

The examples illustrate the effectiveness of Dyruvate to inhibit free-radical production. The clofibrate-fed rats will chronically generate free-radicals. Clofibrate-feeding induced hepatomegaly with an increase in hepatic protein content. Peroxisomal proliferation by electron microscopic evaluation, had a five-fold increase in peroxisomal beta-oxidation activity, an indicator of peroxisomal proliferation and hydrogen peroxide production. The auto-generated hepatic catalase, which detoxifies hydrogen peroxide, increased two-to three-fold. Lipofuscin-like products, i.e., the end-products of free-radical-induced lipid peroxidation, increased by three-fold in the clofibrate-fed animals. These findings suggest free-radical production and hydrogen peroxide production are in agreement with previous investigators.

The rat tests herein reported establish that pyruvate inhibits free-radical generation. Clofibrate-feeding manifests a chronic, free-radical production. Clofibrate-feeding induces hepatomegaly with an increase in hematic protein content, peroxisomal proliferation by electron microscope evaluation and five-fold increase in peroxisomal beta-oxidation activity, a marker of peroxisomal proliferation and hydrogen peroxide production. The total hepatic catalase, which detoxifies hydrogen peroxide, increased by two-to-three fold. Lipofuscin-like products, which are end products from free- radical-induced livid peroxidation, increased by three-fold in the clofibrate-fed animals. These findings, suggestive of hydrogen peroxide production and toxic, free-radical metabolic effects, are in agreement with previous investigations.

In contrast, supplementing the clofibrate-fed animals with vitamin E had no effect on hepatic size, protein content, peroxisomal proliferation or beta-oxidation activity. These findings indicate that free-radical production continued unabated with clofibrate-feeding despite supplementation with vitamin E. However the antioxidant vitamin E, as expected, did reduce the effects of free-radicals on lipid peroxidation; i.e., Vitamin E appeared to be an effective scavenger of free-radicals.

The data suggest that pyruvate has reproducible effects on free-radical generation and subsequent lipid peroxidation. Pyruvate seems to offer promise in the control of the metabolic effects of free-radicals, as a known inhibitor of free-radical production. Vitamin E did not influence free-radical generation.

Pyruvate supplementation of a diet inhibits peroxisomal proliferation and free-radical generation induced by clofibrate. The pyruvate supplementation also inhibits free-radical-induced lipid peroxidation and enhances metabolism of nitric oxide.

ALTERNATIVE TEST RESULTS

Superoxides ($O_2^{0-}$) can be detected by lucigenin-enhanced chemiluminescence (Caraceni, P. et al, J. Am. Physiol. 266, G799-G808, 1994). Superoxides themselves are free-radicals and are known to be a precursor of hydrogen peroxide which is a precursor of other free-radicals.

For example:

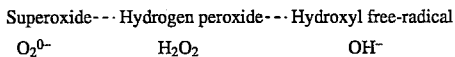

Superoxide --- Hydrogen peroxide --- Hydroxyl free-radical
$O_2^{0-}$       $H_2O_2$           $OH^-$ Both the Superoxide and the hydroxyl are free-radicals, known to be harmful. Pyruvate is known as a scavenger for hydroxyl free- radicals. It is here reported that pyruvate also inhibits the generation of superoxide which thereby lowers the proliferation of objectionable hydroxyl free-radicals.

In the reported experiments, hepatocytes were recovered from adult male Sprague-Dawley rats and centrifuged in appropriate solutions for ten minutes at 1,200 G. Cell viability ranged from 90% to 97%. Cells were embedded in Agarose gel threads, 0.5 mm diameter.

All of the Agarose gel threads were perfused for one hour in KHB (standard Krebs-Henseleit bicarbonate buffer) at 37° C. Thereafter the hepatocytes were segregated into three groups:

1. Control—perfused with KHB solution containing 5 mM glucose.
2. Pyruvate (1)—same as Control containing in addition 1.0 mM pyruvate.
3. Pyruvate (5)—same as Control containing in addition 5.0 mM pyruvate. Each of the groups (1), (2), (3) was rendered anoxic for two hours in anoxic conditions nitrogen by volume and 5% carbon dioxide by volume.

After two hours of anoxia, the nitrogen was replaced with oxygen air restored (reoxygenation) while all cells were perfused with KHB solution.

Figure 4:
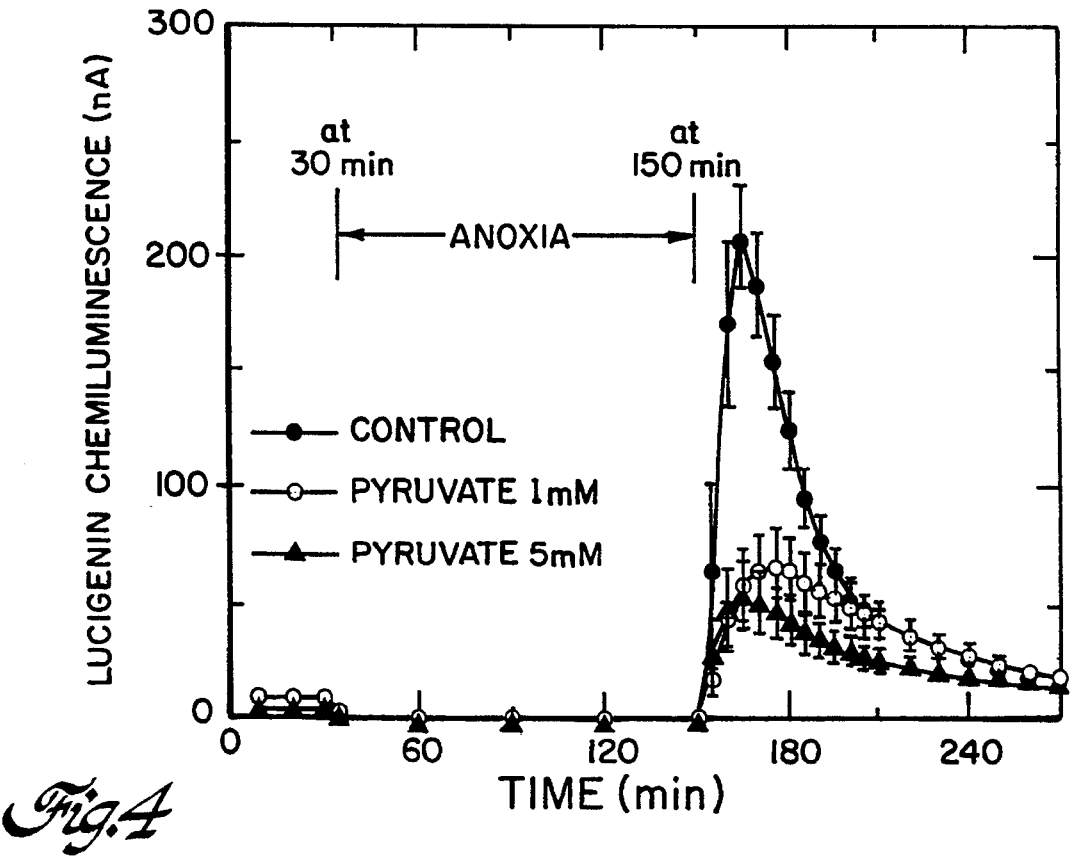
FIG. 4 illustrates lucigenin chemiluminescence, a measure of superoxide for those groups of rat hepatocytes.

The generation of superoxides from the three groups is illustrated in FIG. 4 where the superoxide generation is indicated by the measured lucigenin chemiluminescence in nA. During the two hours of anoxia, lucigenin chemiluminescence ceased for all groups, indicating no superoxide generation. Non-generation of superoxides is expected during anoxia, i.e., the absence of oxygen. Reoxygenation started at 150 minutes (FIG. 4) and the control group (black circles) generated lucigenin chemiluminescence at more than 200 nA. The lucigenin chemiluminescence for the two pyruvate groups (white circles and black triangles) was significantly lower during the reoxygenation period from 150 to 270 minutes. There were six control specimens, six specimens with five mM pyruvate and five specimens with one mM pyruvate. These data indicate that pyruvate inhibits formation of superoxide ($O_2^{0-}$) and hence inhibits free-radical generation.

I claim:

1. The method for inhibiting free-radical generation and concurrently scavenging internally generated-free radicals in a mammal in need thereof comprising administering to said mammal a therapeutically effective quantity of pyruvate.

2. The method of claim 1 wherein said pyruvate is orally fed to said mammal.

3. The method of claim 1 wherein said pyruvate comprises from 5 to 20 weight percent of said mammal's daily energetic intake.

4. The method of claim 1 wherein said pyruvate is sodium pyruvate or calcium pyruvate or a pharmaceutically acceptable ester of pyruvic acid or mixtures thereof.

5. The method of claim 1 wherein said pyruvate is administered to the mammal parenterally.

6. The method of claim 5 wherein the pyruvate is a pharmaceutically acceptable ester of pyruvic acid in aqueous solutions.

7. The method of claim 1 where the pyruvate is administered continuingly to the mammal following an incident which results in excess free-radical generation.

\* \* \* \* \*